United States Patent [19]

Huff et al.

[11] Patent Number: 4,505,918

[45] Date of Patent: * Mar. 19, 1985

[54] 4-[2-PYRIDINYLTHIO(OXY OR AMINO)METHYL]-1H-IMIDAZOLES AND DERIVATIVES

[75] Inventors: Joel R. Huff, Lederach; Walfred S. Saari, Lansdale; John J. Baldwin, Gwynedd Valley, all of Pa.

[73] Assignee: Merck & Co., Inc., Rahway, N.J.

[ * ] Notice: The portion of the term of this patent subsequent to Mar. 19, 2002 has been disclaimed.

[21] Appl. No.: 439,698

[22] Filed: Nov. 8, 1982

[51] Int. Cl.$^3$ .................. C07D 401/12; A61K 31/415
[52] U.S. Cl. ..................................... 514/341; 546/278
[58] Field of Search ..................... 546/278; 424/263

[56] References Cited

U.S. PATENT DOCUMENTS

| | | | |
|---|---|---|---|
| 3,907,816 | 9/1975 | Winkelmann et al. | 548/278 |
| 4,046,896 | 9/1977 | Winkelmann et al. | 548/278 |
| 4,078,063 | 3/1978 | Lumma et al. | 424/250 |
| 4,376,772 | 3/1983 | Saari et al. | 424/250 |
| 4,381,302 | 4/1983 | Huff et al. | 424/250 |
| 4,442,103 | 4/1984 | Saari | 424/250 |
| 4,456,604 | 6/1984 | Saari | 424/250 |

OTHER PUBLICATIONS

Ser. No. 439,697, by Huff et al.
Ser. No. 436,753, by Saari.

*Primary Examiner*—Jane T. Fan
*Attorney, Agent, or Firm*—William H. Nicholson

[57] ABSTRACT

4-[2-Pyridinylthio(oxy or amino)methyl]-1H-imidazoles and derivatives and acid addition salts thereof are selective central-adrenergic receptor agonists and thereby useful as antihypertensives.

3 Claims, No Drawings

4-[2-PYRIDINYLTHIO(OXY OR AMINO)METHYL]-1H-IMIDAZOLES AND DERIVATIVES

BACKGROUND OF THE INVENTION

This invention is concerned with novel 4-[2-pyridinylthio(oxy or amino)methyl]-1H-imidazoles and derivatives or pharmaceutically acceptable salts thereof of structural Formula I

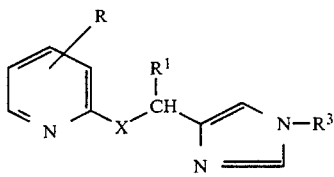

which have antihypertensive activity. It also relates to a process for preparing the novel compounds, pharmaceutical compositions comprising the novel compounds and to a method of treating hypertension with the novel compounds.

The pyridine group is common among compounds with useful pharmacological properties, such as the 2-piperazinyl-5 (and/or 6)-substituted pyridines of U.S. Pat. No. 4,078,063 which are anorexigenic agents and also said to have antidepressant activity by virtue of their pharmacological influence on serotonin levels.

Now, with the present invention there is provided a group of substituted pyridines of structural Formula I which are antihypertensive by virtue of their ability to stimulate central-adrenergic receptor sites.

DETAILED DESCRIPTION OF THE INVENTION

This invention is concerned with compounds of structural formula I:

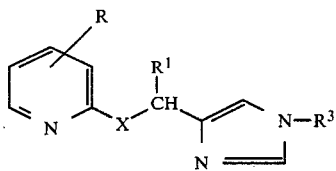

or a pharmaceutically acceptable salt thereof, wherein
R is
1. hydrogen,
2. halo such as fluoro, chloro, bromo or iodo, especially fluoro or chloro,
3. $C_{1-3}$alkyl such as methyl, ethyl or propyl,
4. hydroxy,
5. $C_{1-3}$alkoxy such as methoxy, ethoxy or propoxy,
6. phenyl-$C_{1-3}$alkoxy, especially benzyloxy,
7. $C_{3-5}$alkenyloxy, especially allyloxy,
8. di($C_{1-3}$alkyl) amino, especially dimethylamino,
9. nitro,
10. trifluoromethyl,
11. sulfonamido,
12. N,N-di ($C_{1-3}$alkyl) sulfonamido, and
13. $C_{2-5}$alkanoyl, especially acetyl;
X is

—S—, >SO, >$SO_2$ or —O—; and $R^1$, $R^2$ and $R^3$ are independently hydrogen or $C_{1-3}$ alkyl.

It is preferred that R be fluoro or chloro. It is further preferred that X be —S—.

The pharmaceutically acceptable salts coming within the purview of this invention include the pharmaceutically acceptable acid-addition salts. Acids useful for preparing these acid-addition salts include inter alia, inorganic acids, such as the hydrohalic acids (e.g., hydrochloric and hydrobromic acid), sulfuric acid, nitric acid, and phosphoric acid, and organic acids such as maleic, fumaric tartaric, citric, acetic, benzoic, 2-acetoxybenzoic, salacylic, succinic acid, theophylline, 8-chlorotheophylline, p-aminobenzoic, p-acetamidobenzoic, methanesulfonic, or ethane disulfonic.

The novel compounds of this invention are prepared in accordance with the following general Reaction Scheme I:

REACTION SCHEME I

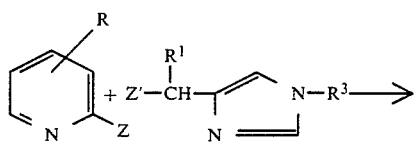

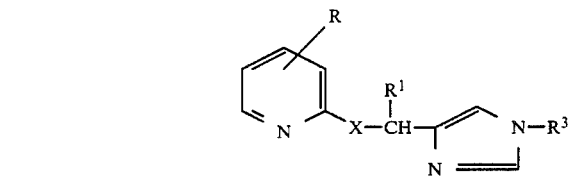

wherein Z and Z' are XH and Y respectively or Z and Z' are Y and XH respectively.

More specifically, the process is represented by Reaction Scheme Ia or Ib.

REACTION SCHEME IA

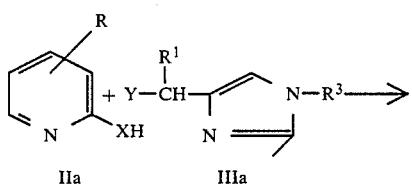

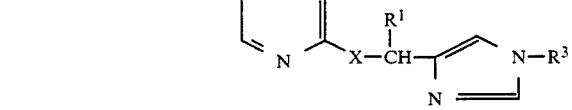

REACTION SCHEME IB

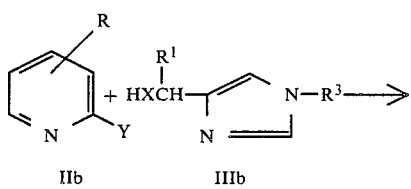

wherein R, and $R^1$ are as previously defined, X is $$-\underset{\underset{\textstyle -N-}{|}}{\overset{R^2}{}}$$

—S—, or —O—, and Y is halogen, especially chloro, $C_{1-5}$alkylsulfonyloxy, such as methanesulfonyloxy; or benzenoid arylsulfonyloxy such as, benzenesulfonyloxy or toluenesulfonyloxy.

The reaction is conducted in an inert organic solvent such as a $C_{1-4}$alkanol, preferably methanol, or acetonitrile, dimethylformamide, dimethylsulfoxide or hexamethylphosphoramide, in the presence of a strong base such as an alkali metal hydride or alkali metal $C_{1-4}$alkoxide, for example sodium hydride or potassium tert-butoxide.

There are employed temperatures ranging from about 15° C. to about 100° C., preferably under anhydrous conditions until a substantial amount of desired compound of Formula I is obtained, typically for a period of from about 2 to about 24 hours, preferably from about 3 to 20 hours.

The compounds in which X is $>SO$ or $>SO_2$ are prepared by treating the corresponding sulfide with a peracid in a strongly acidic medium, such as peroxytrifluoroacetic acid in trifluoroacetic acid medium at about −10° C. to about +10° C.

In the novel method of treating hypertension a novel compound or pharmaceutically acceptable salt thereof is administered in an amount ranging from about 0.01 to about 20 mg per kg of body weight per day, preferably from about 0.1 to about 10 mg per kg of body weight per day in a single dose or in 2 to 4 divided doses.

The compounds, or pharmaceutically acceptable salts thereof, of the present invention, in the described dosages, are administered orally, intraperitoneally, subcutaneously, intramuscularly or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The following examples illustrate the present invention without, however, limiting the same thereto.

EXAMPLE 1

4-[3-Chloro-2-pyridinyloxymethyl]-1-methyl-1H-imidazole Hydrochloride

4-Hydroxymethyl-1-methyl-1H-imidazole hydrochloride (2.18 g, 14.5 mmol) is added to a stirred slurry of sodium hydride (1.49 g of a 50% dispersion in mineral oil, 31 mmol, previously washed with pentane and dried under nitrogen) and dimethylformamide, 70 ml. After 15 minutes, a solution of 2,3-dichloropyridine (2.22 g, 15 mmol) in 10 ml of dimethylformamide is added and stirring is continued for 3 hours. The reaction mixture is then poured into 150 ml of water, and extracted with three 90 ml portions of ethyl acetate. The ethyl acetate extracts are combined, dried over anhydrous magnesium sulfate, filtered and concentrated to an oil which is purified by flash chromatography over silica gel 60 (230–400 mesh) by elution with 10% methanol-90% chloroform saturated with ammonia. The purified base is dissolved in ethanol, treated with an ethanolichydrogen chloride solution and the hydrochloride salt is precipitated with diethyl ether.

Employing the procedure substantially as described in Example 1, but substituting for the 2,3-dichloropyridine and the 4-hydroxymethyl-1-methyl-1H-imidazole used therein, equimolecular amounts of 2-chloro-3-R-pyridine and 4(5)-hydroxy-($R^1$)methyl-1-methyl-1H-imidazole respectively, there are produced the 4(5)-[3-R-2-pyridinyloxy($R^1$)methyl]-1-methyl-1H-imidazoles described in Table I:

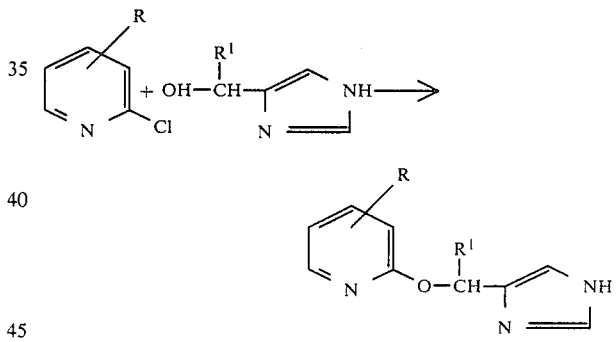

TABLE I

| R | $R^1$ |
|---|---|
| H | H |
| 3-F | H |
| 3-F | —CH$_3$ |
| 3-Br | H |
| 3-OCH$_3$ | H |
| 3-OCH$_2$C$_6$H$_5$ | H |
| 3-CH$_3$ | H |
| 3-OCH$_2$—CH=CH$_2$ | H |
| 5-NO$_2$ | H |
| 5-N(CH$_3$)$_2$ | H |
| 3-CF$_3$ | H |
| 3-SO$_2$NH$_2$ | H |
| 3-SO$_2$N(CH$_3$)$_2$ | H |
| 5-COC$_2$H$_5$ | H |

EXAMPLE 2

4-(3-Chloropyridin-2-ylthiomethyl)-1H-imidazole maleate

To a suspension of sodium hydride (0.94 g, 19.6 mmol of 50% oil dispersion) in 15 ml of methanol was added 4-(chloromethyl)-1H-imidazole hydrochloride (1.5 g, 9.8 mmol) with cooling in an ice bath. 3-Chloro-2-pyridinethione (1.42 g, 9.8 mmol) was added and the reaction mixture was stirred at room temperature overnight. The reaction was concentrated in vacuo and partitioned between water and methylene chloride. The methylene chloride was washed ($H_2O$), dried ($MgSO_4$), filtered, and concentrated in vacuo to a yellow oil. The oil was chromatographed on silica gel with 2% methanol/chloroform saturated with ammonia. The crude product was treated with maleic acid in isopropanol to yield the hydrogen maleate salt, m.p. 148°–150° C.

Employing the procedure substantially as described in Example 2, but substituting for the 2-thiopyridone and the 4(5)-chloromethyl-1H-imidazole used therein, equimolecular amounts of 3-R-2-thiopyridone and 4(5)-chloro-($R^1$)-methyl-1H-imidazole respectively, there are produced the 4(5)-[3-R-2-pyridinylthio-($R^1$)methyl]-1H-imidazoles described in Table II:

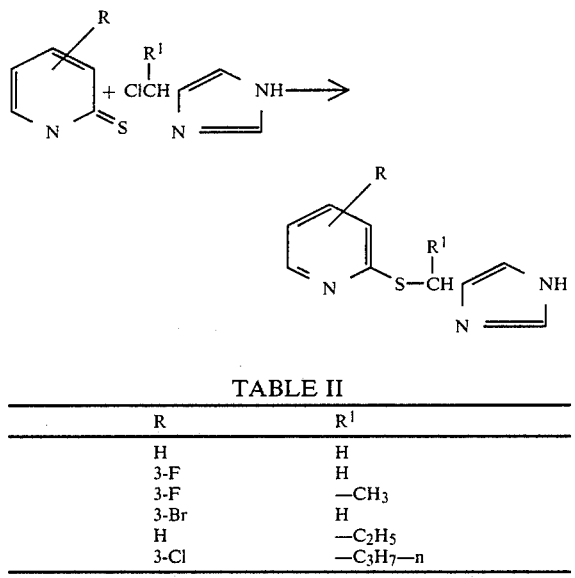

TABLE II

| R | $R^1$ |
|---|---|
| H | H |
| 3-F | H |
| 3-F | —$CH_3$ |
| 3-Br | H |
| H | —$C_2H_5$ |
| 3-Cl | —$C_3H_7$—n |

EXAMPLE 3

4(5)-[3-Chloro-2-pyridinylaminomethyl]-1H-imidazole Hydrogen Maleate

2-Amino-3-chloropyridine (2.6 g, 20 mmol) is added in portions to a stirred slurry of sodium hydride (1.9 g of a 50% dispersion in mineral oil, 40 mmol) in 50 ml of dimethylformamide. After stirring at 20°–25° C. for 1 hour and 65° C. for 1 hour, 4(5)-chloromethyl-1H-imidazole hydrochloride (3.1 g, 20 mmol) is added portionwise. The reaction mixture is stirred at 65° C. for 20 hours and then most of the dimethylformamide is removed under reduced pressure. The residue is mixed with 50 ml of water, acidified by the addition of concentrated hydrochloric acid and extracted with diethyl ether to remove nonbasic material. The aqueous extract is made basic with a 40% sodium hydroxide solution and the product extracted into diethyl ether. After washing the ether extract with a saturated sodium chloride solution, the ether layer is dried over anhydrous sodium sulfate, filtered and concentrated. This crude product is purified further by flash chromatography over silica gel 60 (230–400 mesh) and elution with 1% methanol-99% chloroform saturated with ammonia. The product is dissolved in ethanol, treated with an equivalent of maleic acid, and the hydrogen maleate salt of 4(5)-b [3-chloro-2-pyridinylaminomethyl]-1H-imidazole, is precipitated with ethyl acetate.

Employing the procedure substantially as described in Example 3, but substituting for the 2-amino-3-chloropyridine and the 4(5)-chloromethyl-1H-imidazole used therein, equimolecular amounts of 2-($R^2$ amino)-3-R-pyridine and 4(5)-chloro ($R^1$)methyl-1H-imidazole, respectively, there are produced the 4(5)-[3-R-2-pyridinyl-N-$R^2$-amino($R^1$)methyl]-1H-imidazoles described in Table III.

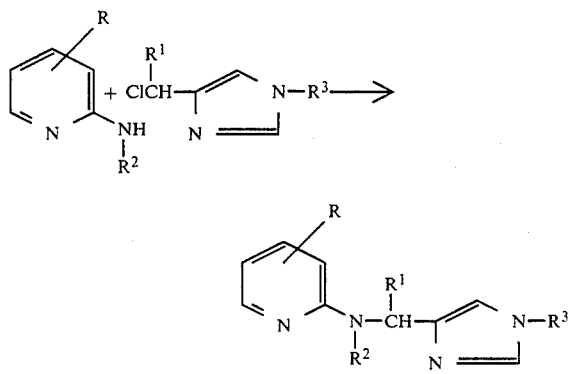

TABLE III

| R | $R^1$ | $R^2$ | $R^3$ |
|---|---|---|---|
| H | H | H | H |
| 3-F | H | H | —$CH_3$ |
| 5-F | —$CH_3$ | H | H |
| 3-Br | H | H | —$CH_3$ |
| 3-F | H | —$CH_3$ | H |
| 3-Cl | —$C_2H_5$ | H | H |
| H | H | —$C_2H_5$ | —$CH_3$ |
| H | H | —$C_2H_7$—n | H |
| 5-$CH_3$ | H | $CH_3$ | H |

EXAMPLE 4

4-(3-Chloro-2-pyridinylthiomethyl)-1-methyl-1H-imidazole dihydrochloride

To a solution of sodium (90.6 mg, 3.94 mmol) in 10 ml of ethanol was added 3-chloro-2-thiopyridine (286 mg, 1.97 mmol) and the reaction was stirred ten minutes. A solution of 4-(chloromethyl)-1-methyl-1H-imidazole hydrochloride (330 mg, 1.97 mmol) in 5 ml of ethanol was added dropwise and the reaction was stirred at room temperature overnight. The reaction was concentrated in vacuo, and partitioned between saturated sodium carbonate and chloroform. The chloroform solution was dried ($MgSO_4$), filtred and concentrated in vacuo to a brown oil. The oil was chromatographed on silica gel with chloroform saturated with ammonia. The crude product was treated with ethanolic hydrogen chloride to yield the dihydrochloride salt of the product, m.p. 143°–146° C.

Employing the procedure substantially as described in Example 4, but substituting for the 2-thiopyridone and the 4-chloromethyl-1-methyl-1H-imidazole used therein, equimolecular amounts of 3R-2-thiopyridone and 4-chloro-($R^1$)-methyl-1-methyl-1H-imidazole respectively, there are produced the 4-[3-R-2-pyridinylthio-($R^1$)-methyl]-1-methyl-1H-imidazoles described in Table IV:

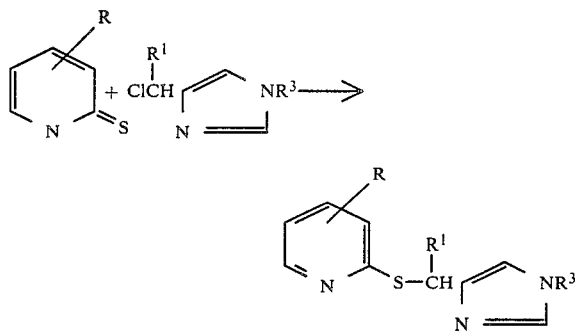

TABLE IV

| R | R¹ |
|---|---|
| H | H |
| 3-F | H |
| 3-F | —CH₃ |
| 3-Br | H |
| H | —C₂H₅ |
| 3-Cl | —C₃H₇—n |

EXAMPLE 5

4-(3-Chloro-2-pyridinylsulfinylmethyl)-1H-imidazole hydrogen oxalate

In a 25 ml, three necked, round-bottomed flask, outfitted with a magnetic stirrer, thermometer, and addition funnel is placed trifluoroacetic acid (5 ml) and 4-(3-chloro-2-pyridylthiomethyl)-1H-imidazole (1.5 g; 6.6 mmol). Peroxytrifluoroacetic acid (1.65 ml; 6.6 mmol), from a stock solution prepared by mixing 8.6 ml of 30% hydrogen peroxide and trifluoroacetic acid to a final volume of 25 ml to give a 4M solution of the peracid, is added dropwise to the stirred, cooled (0°) sulfide mixture. The reaction is kept at 0° until the peroxide is discharged (starch-iodide paper) and the starting material is consumed. Solvent is removed in vacuo and the residue dissolved in methylene chloride, washed with 5% sodium hydroxide, and dried (Na₂SO₄). Removal of the solvent affords the sulfoxide which is crystallized as its hydrogen oxalate salt.

EXAMPLE 6

4-(3-Chloro-2-pyridylsulfonylmethyl)-1H-imidazole hydrogen oxalate

This compound is prepared by following the procedure of Example 5 employing 2.0 equivalents of peroxytrifluoroacetic acid.

EXAMPLE 7

| Pharmaceutical Formulation | Mg/Capsule |
|---|---|
| Active Ingredient | 6 |
| Starch | 87 |
| Magnesium stearate | 7 |

The active ingredient, starch and magnesium stearate are blended together. The mixture is used to fill hard shall capsules of a suitable size at a fill weight of 100 mg per capsule.

What is claimed is:

1. A compound of structural formula

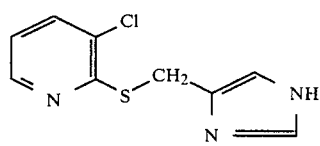

or a pharmaceutically acceptable salt thereof.

2. An antihypertensive pharmaceutical formulation comprising a pharmaceutical carrier and an effective amount of the compound of claim 1 or a pharmaceutically acceptable salt thereof.

3. A method of treating hypertension comprising the administration to a patient in need of such treatment of an effective amount of the compound of claim 1 or a pharmaceutically acceptable salt thereof.

* * * * *